United States Patent [19]

Yasuhara et al.

[11] Patent Number: 4,987,260

[45] Date of Patent: * Jan. 22, 1991

[54] PREPARATION OF ANILINES

[75] Inventors: Mitsuki Yasuhara; Fujihisa Matsunaga, both of Ichihara, Japan

[73] Assignee: Mitsui Petrochemical Industries, Ltd., Tokyo, Japan

[ * ] Notice: The portion of the term of this patent subsequent to Jan. 22, 2008 has been disclaimed.

[21] Appl. No.: 283,846

[22] Filed: Dec. 13, 1988

[30] Foreign Application Priority Data

Dec. 18, 1987 [JP] Japan .................................. 62-320806

[51] Int. Cl.$^5$ ............................................ C07C 209/18
[52] U.S. Cl. ..................................... 564/402; 502/355; 564/395
[58] Field of Search .......................................... 564/402

[56] References Cited

U.S. PATENT DOCUMENTS

| 3,272,865 | 9/1966 | Barker | 564/402 |
| 3,860,650 | 1/1975 | Becker et al. | 564/402 |
| 4,496,763 | 1/1985 | LeBlanc et al. | 564/402 |

FOREIGN PATENT DOCUMENTS

| 42-23571 | 11/1967 | Japan | 564/402 |
| 46-23052 | 7/1971 | Japan | 564/402 |
| 46-23053 | 7/1971 | Japan | 564/402 |
| 48-67229 | 4/1973 | Japan | 564/402 |
| 4014737 | 4/1974 | Japan | 564/402 |
| 8803920 | 6/1988 | PCT Int'l Appl. | 564/402 |

Primary Examiner—Richard L. Raymond
Assistant Examiner—Susan P. Treanor
Attorney, Agent, or Firm—Nixon & Vanderhye

[57] ABSTRACT

An aniline is prepared by reacting a phenol with an amination agent in the presence of a specific porous γ-alumina catalyst.

2 Claims, 3 Drawing Sheets

PREPARATION OF ANILINES

BACKGROUND OF THE INVENTION

This invention relates to the preparation of anilines, more particularly, to a process for preparing an aniline at high conversion and high selectivity by reacting a phenol with an amination agent in the presence of a specific catalyst while maintaining the catalytic activity for an extended period of time.

Anilines are a group of chemicals of industrial importance finding use as rubber vulcanization promotors, dyes, mordants, medicines, explosive stock, and starting material for diphenylmethane diisocyanate (MDI). Aniline derivatives such as toluidine, cumidine, methylcumidine, and xylidine recently find increasing utility as starting materials for photographic agents, agricultural agents, and medicines.

These anilines are produced in the prior art by (1) reducing aromatic nitro compounds with hydrogen, (2) reacting halogenated aromatic compounds with aqueous ammonia at elevated temperatures under a certain pressure, and (3) reacting phenols with ammonia.

The first method (1) using aromatic nitro compounds requires a great quantity of sulfuric acid or nitric acid as the agent for nitrating aromatic compounds, which is followed by a neutralizing step requiring a great quantity of alkali such as sodium hydroxide. There is yielded water containing salts in high concentrations. In addition, as indicated in Japanese Patent Application Kokai No. 48-67229, nitrogen oxide gases evolve during the step of forming nitro compounds, causing air pollution. In nitrating alkylphenols, there are produced a variety of isomeric by-products in addition to the desired nitro compound. These isomers are difficult to isolate. It is thus difficult to produce pure anilines in high yields.

The second method (2) using halogenated aromatic compounds has a critical problem that an expensive corrosion-resistant equipment must be installed for the preparation of halogenated aromatic compounds because very highly corrosive chlorine is used therefor. It is known that reaction between chlorobenzene and ammonia results in low yields despite elevated temperature and pressure. This method is seldom utilized in the art except when the halogenated aromatic compound is p-nitrochlorobenzene having a nitro group at the para-position of chlorobenzene.

In contrast to methods (1) and (2), the third method (3) based on reaction of phenols with ammonia currently draws attention and becomes a mainstream process for the preparation of anilines. This method enables to produce anilines merely by passing phenols and ammonia through a fixed bed of catalyst. This method has many advantages because it is a very simple process which does not yield nitrogen oxide gases causing air pollution or a great amount of water.

A typical method for the preparation of anilines by reaction of phenols with ammonia is disclosed in Japanese Patent Publication No. 42-23571. According to the disclosed method, aminated benzenes such as aniline are prepared by reacting a hydroxybenzene such as phenol with an amination agent in the presence of a catalyst selected from the group consisting of silica-alumina, zirconia-alumina, titania-alumina, zirconia-silica phosphates and tungstates at a temperature of 300° to 600° C. This publication teaches that weakly acidic solid acids such as γ-alumina catalysts are insufficient because of low activity, but a silica-alumina catalyst which is a strongly acidic solid acid is fully effective as the catalyst for such amination reaction.

The use of strongly acidic solid acid catalysts such as silica-alumina catalyst, however, undesirably invites side reactions including decomposition of anilines and formation of resinous by-products although these acid catalysts have high initial activity for amination reaction. These catalysts have a critical problem that once such a resinous substance is deposited on the catalyst surface, the catalyst undergoes rapid deactivation because active sites are covered with the resinous deposit. Thus the catalyst must be frequently regenerated.

One attempt to solve these problems is proposed in Japanese Patent Application Kokai No. 48-67229, in which reaction of phenol with an amination agent is carried out using a catalyst having a lower acid strength than the above-mentioned silica-alumina catalyst (pKa<−8.0), that is, titania-zirconia and titania-silica catalysts which are solid acid catalysts having an acid strength in the range of pKa−5.6 to −3.0. Even with the use of such catalysts, the reaction temperature must be increased to as high as 400° to 500° C. in order to accomplish effective amination reaction. The elevated reaction temperature accelerates decomposition of the amination agent or ammonia, producing nitrogen according to the following scheme:

$$NH_3 \rightarrow \tfrac{1}{2}N_2 + 3/2H_2$$

The reactor undergoes embrittlement with nascent nitrogen. Undesirably, the effective life of the reactor is significantly reduced. It is also observed that the catalyst suddenly loses its activity within a time as short as about 40 hours. For these reasons, this method is very difficult to commercially practice.

Japanese Patent Application Kokai No. 46-23052 discloses amination of phenols using a combined catalyst comprising a dehydrating solid acid catalyst combined with a hydrogenating catalyst. Japanese Patent Application Kokai No. 46-23053 discloses amination of phenols using a catalyst comprising alumina or silica combined with an oxide selected from magnesia, boria and thoria. In either case, the activity sustaining time is improved to only 50 to 100 hours, leaving the catalyst deactivation problem unsolved.

In summary, the prior art known methods for preparing anilines by amination of phenols require high temperatures of at least 400° C. in order to accomplish effective amination reaction, which in turn, induces decomposition of the amination agent or ammonia, causing embrittlement of the reactor with nascent nitrogen. These methods also suffer from the critical problem of frequent catalyst regeneration because the catalytic activity is shortly lost due to contamination of the catalyst surface by a resinous substance resulting from decomposition of anilines or coverage of the catalyst surface with a carbonaceous deposit resulting from decomposition of an organic substance.

SUMMARY OF THE INVENTION

It is therefore an object of the present invention to provide a novel and improved process for preparing an aniline by reacting a phenol with an amination agent using a specific catalyst, thereby enabling preparation of the aniline in high yields, with high selectivity and at a relatively low reaction temperature.

Another object of the present invention is to provide a novel and improved process for preparing an aniline by reacting a phenol with an amination agent in the presence of a specific catalyst while sustaining the catalytic activity.

According to the present invention, there is provided a process for preparing an aniline, comprising reacting a phenol with an amination agent in the presence of a γ-alumina catalyst having a mean pore diameter in the range of from 30 to 90 angstroms with a standard deviation (σn) of 10 to 40 angstroms based on statistic calculation from pore diameter and pore volume.

Preferably, the γ-alumina catalyst contains ink bottle-shaped pores in a total pore volume of at least 0.4 c.c./gram on dry basis.

Also preferably, the γ-alumina catalyst is a weakly acidic low alkali alumina having a pKa value in the range of from +3.3 to +6.8 as measured with Hammett's indicator and an integrated acid quantity of up to 0.5 meq/gram on dry basis and consisting essentially of at least 90% by weight of alumina, less than 10% by weight of silica, and up to 0.5% by weight of an alkali metal oxide in dry state.

Since the present process uses a specific γ-alumina catalyst as defined above, anilines can be produced at higher conversion and higher selectivity even when reaction is made at a lower temperature than with the prior art catalysts. In addition, the activity of the catalyst is maintained over an extended period of time.

BRIEF DESCRIPTION OF THE DRAWINGS

The above and other objects, features, and advantages of the present invention will be better understood from the following description taken in conjunction with the accompanying drawings, in which.

DETAILED DESCRIPTION OF THE INVENTION

Figure 1:
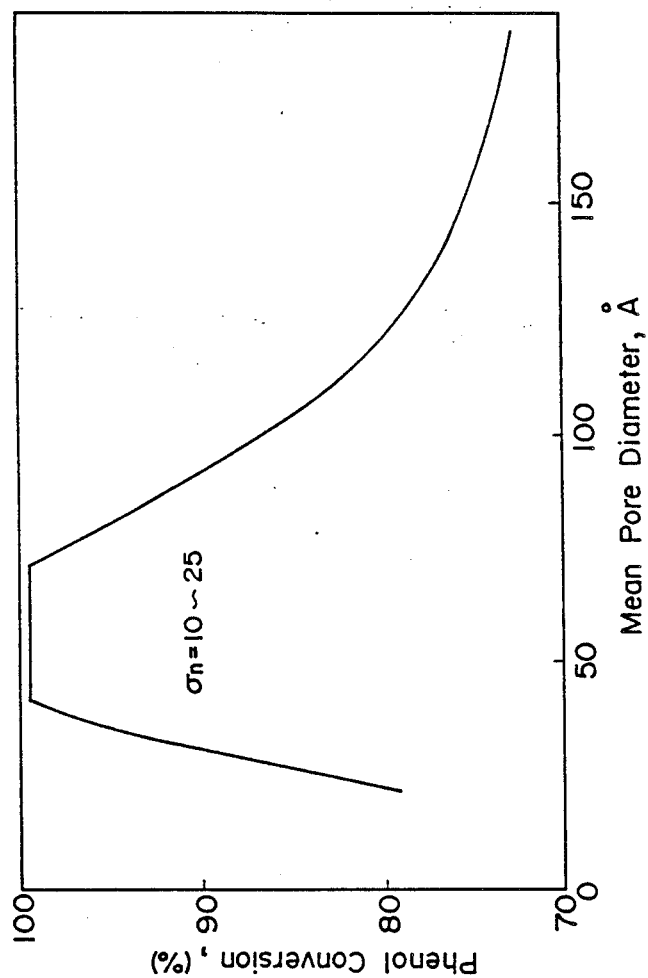
FIG. 1 is a diagram showing the conversion of phenol as a function of the mean pore diameter of catalyst with a standard deviation (σn) of 10 to 25.

The phenols, amination agents, and catalysts used in the process of the present invention are described in detail.

Phenols

According to the process of the present invention, anilines are prepared by reacting phenols with amination agents. The phenols used as one reactant in the present process include phenol, alkylphenols such as cresol, o-, m- and p-isomers of ethylphenol and isopropylphenol, and alkylphenols having at least one alkyl substituent, for example, such as dimethylphenol, methylethylphenol, methylisopropylphenol, methylbutylphenol, diethylphenol, ethylisopropylphenol, ethylbutylphenol, diisopropylphenol, isopropylbutylphenol, and dibutylphenol. Also included are mixtures of phenol and alkyl phenols in any proportion. Phenol is most preferred among these phenols.

Amination agent

The amination agents which may be used herein for reaction with the foregoing phenols include ammonia, ammonia-generating compounds, and organic amines. The ammonia-generating compounds are those inorganic compounds which generate ammonia gas upon thermal decomposition, for example, ammonium carbonate and ammonium sulfate. Examples of the organic amines include methylamine, ethylamine, n-propylamine, dimethylamine, diethylamine, dipropylamine, methylethylamine, cyclohexylamine, aminopyridine, aniline, methylaniline, ethylaniline, n-propylaniline, isopropylaniline, dimethylaniline, diethylaniline, dipropylaniline, methylethylaniline, and methylpropylaniline. Ammonia is most preferred.

Catalyst

The catalyst used herein is a porous γ-alumina catalyst having a specific pore distribution, that is, having a mean pore diameter in the range of from 30 to 90 angstroms with a standard deviation (σn) of 10 to 40 angstroms based on statistic calculation from pore diameter and pore volume. The γ-alumina catalyst having such a specific pore distribution is used for the following reason.

For the purpose of developing a catalyst which has substantially higher activity than prior art conventional catalysts and a longer effective life in that it can sustain its catalytic activity for an extended period of time, we have investigated a number of alumina catalysts for their correlation between physical properties and catalytic activity. No correlation is observed between catalytic activity and those factors which were believed to govern catalytic activity in the prior art, for example, specific surface area, acid strength distribution, and adsorptivities including ammonia adsorptivity, pyridine adsorptivity, and dehydrating ability. Surprisingly, we have found a definite correlation between catalytic activity and pore distribution which was neglected in the prior art. The present invention is predicated on this finding.

The pore distribution used herein is a distribution representative of the relationship between a pore diameter (2r) and a corresponding pore volume, that is, a proportion of an infinitesimal change of pore volume (dV) relative to an infinitesimal change of pore radius (dr), dV/dr, which can be determined by an analysis of isothermal adsorption/desorption curves of nitrogen gas at the temperature of liquid nitrogen by Cranston-Inkey method.

Provided that the pore distribution is a statistic distribution, the catalytic activity depends on the mean pore diameter which means the diameter across which pores are centrally distributed on average as well as the standard deviation (σn) which means the width of distribution of the pore diameter.

FIG. 1 shows how the mean pore diameter of a catalyst is correlated to the conversion of phenol representative of catalytic activity. This curve is obtained by reacting phenol with ammonia in the presence of γ-alumina catalysts having variable pore distribution under a given set of reaction conditions including a liquid hourly space velocity (LHSV) of phenol of 0.045 hr$^{-1}$, a molar ratio of ammonia to phenol of 16, a reaction pressure of 15 kg/cm$^2$-G, and a reaction temperature of 370° C.

As seen from the curve of FIG. 1, for those γ-alumina catalysts having a standard deviation (σn) of 10 to 25 Å, the preferred mean pore diameter is in the range of from 30 to 90 Å, especially from 40 to 70 Å. With a mean pore distribution of less than 30 Å or more than 90 Å, the conversion of phenol drastically drops to less than 90%, evidently indicating a loss of catalytic activity.

It is then described how catalytic activity depends on the standard deviation ($\sigma n$) of the pore distribution of a catalyst. With a mean pore diameter falling within the above-mentioned range, a standard deviation ($\sigma n$) range of up to 40 Å indicating a very sharp distribution of pore diameter ensures that the catalytic activity reaches the desired level which corresponds to a phenol conversion of at least 90% at 370° C. Therefore, the preferred range of standard deviation ($\sigma n$) is from 10 to 40 Å, especially from 10 to 30 Å.

With respect to pore distribution, the $\gamma$-alumina catalyst used in the present invention should have a mean pore diameter of from 30 to 90 Å and a standard deviation ($\sigma n$) of pore distribution of from 10 to 40 Å as described above. Preferably, higher catalytic activity is achieved when the catalyst contains pores in a total pore volume of at least 0.4 c.c./gram on dry basis.

The reason why the selectivity and yield of an aniline are significantly improved when a $\gamma$-alumina catalyst having a specific pore distribution as defined above is used in gas phase reaction of a phenol with an amination agent is presumed as follows. The $\gamma$-alumina catalyst used in the present invention has a sharp distribution of pore diameter as represented by a mean pore diameter of from 30 to 90 Å with its standard deviation ($\sigma n$) of from 10 to 40 Å and preferably has a total pore volume as large as 0.4 c.c./gram or more on dry basis. The catalyst has a reduced resistance to diffusion of reactants within pores and offers an increased rate of diffusion, allowing effective contact of reactants with active sites of the catalyst. Because of its increased effective factor, the catalyst is fully active to improve the selectivity and yield of an end aniline. Since the sharply controlled distribution of pore diameter effectively inhibits formation of by-products including highboiling substances having a large size of molecule such as diphenylamine and tar materials, the catalyst will maintain its catalytic activity over an extended period of time.

With the use of a $\gamma$-alumina catalyst having a specific pore diameter, not only the yield of an aniline, but also the selectivity or prevalence of primary reaction over concurrently occurring side reactions are improved. The use of the present catalyst allows reaction to proceed at a lower temperature, assisting in extending the catalyst life.

In one preferred embodiment, the $\gamma$-alumina catalyst has an acid strength distribution such that it has a pKa value in the range of from $+3.3$ to $+6.8$ as measured with Hammett's indicator and an integrated acid quantity of up to 0.5 meq/gram on dry basis. These values suggest the unique feature of the present catalyst that it is weakly acidic as compared with the catalysts for aniline preparation described in the above-cited Japanese Patent Publication Nos. 42-23571 and 47-12341 and Japanese Patent Application Kokai No. 45-67229. In fact, Japanese Patent Publication No. 47-12341 discloses a process for the preparation of anilines using a $\gamma$-alumina catalyst similar to the present catalyst. Measuring the acid strength distribution of the catalyst in the form of Alcoa H-151 (tradename of $\gamma$-alumina commercially available from Alumina Corporation of America, U.S.A.) treated with aqueous boric acid or hydrochloric acid described in Example 2 of Japanese Patent Publication No. 47-12341 using Hammett's indicator, we have found that strong acid sites having a pKa value of less than $-3.0$ are present in an amount as large as 0.4 to 0.5 meq/gram on dry basis, indicating that the Alcoa catalyst is different from the weakly acidic catalyst according to the present invention. It is quite unexpected that the catalyst according to the present invention has very high catalytic activity despite weak acidity. The weak acidity is effective in controlling degradation of an end aniline and formation of resinous by-products, thus constituting one factor contributing to extention of the catalyst lifetime.

The $\gamma$-alumina catalyst used herein and defined above is preferably a low alkali alumina consisting essentially of at least 90% by weight of alumina, less than 10% by weight of silica, and up to 0.5% by weight of an alkali metal oxide in dry state.

Figure 2A:
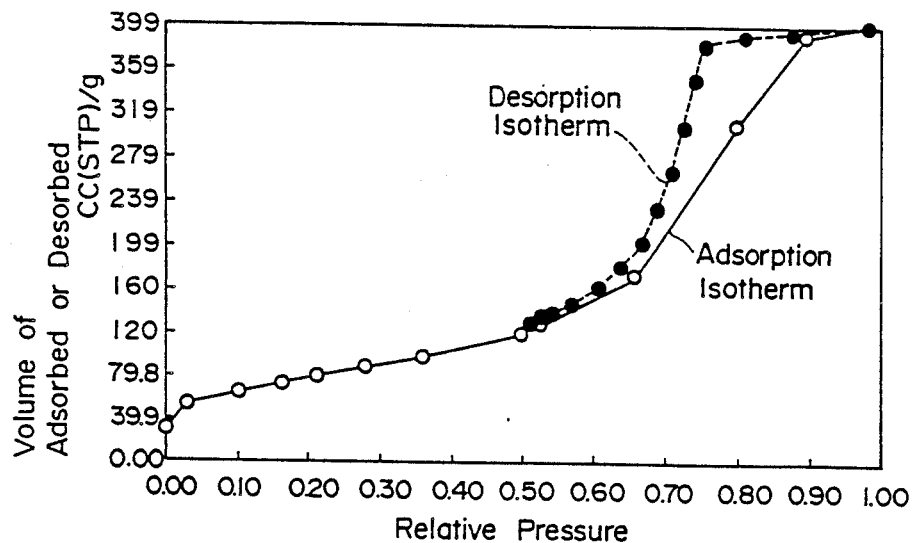
FIGS. 2a and 2b are diagrams showing isothermal nitrogen adsorption/desorption curves of typical catalysts according to the present invention and the prior art, respectively.

The $\gamma$-alumina catalyst used herein is also characterized by its pore structure. The present catalyst is apparently different from the catalyst described in the above-cited Japanese Patent Publication No. 47-12341 in this respect too. As seen from FIG. 2a showing the isothermal nitrogen adsorption/desorption curves of a catalyst according to the present invention, the present catalyst exhibits a unique phenomenon that its isothermal desorption curve shows a smaller desorption amount at a high relative pressure and rapidly approaches to the isothermal adsorption curve below the relative pressure corresponding to the radius of a throat portion of a pore. This means that the pore structure of the present catalyst is of typical ink bottle shape.

Figure 2B:
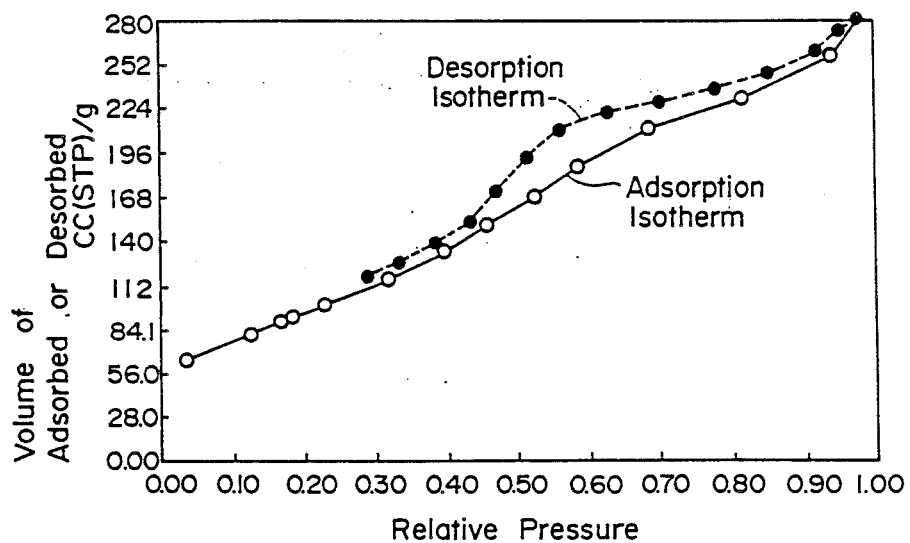

In contrast to the pore structure of the present catalyst, the Alcoa H-151 catalyst treated with aqueous boric acid or hydrochloric acid described in the above-cited Japanese Patent Publication No. 47-12341 has a pore structure of slit shape as understood from the isothermal nitrogen adsorption/desorption curves of FIG. 2b.

The $\gamma$-alumina catalyst of the present invention characterized by a specific pore distribution, low alkali content, weak acidity, and pore structure as defined above may be obtained by mixing sodium aluminate and aluminum sulfate, precipitating aluminum hydroxide from the mixture, and processing the precipitate by washing, aging, jet drying, granulating, drying and other suitable steps so as to control the pore distribution and structure to the desired ones.

Reaction Conditions

In the practice of the present invention, phenols are reacted with amination agents in the presence of a specific low alkali, weakly acidic $\gamma$-alumina catalyst. The reaction conditions applicable herein may be substantially the same as known for the same type of reaction in the prior art.

The reaction temperature is one exception. It may be from about 300° to about 600° C., more preferably from about 300° C. to about 400° C. The present process allows reaction to proceed at a lower temperature than in the prior art.

The reaction pressure may be either atmospheric pressure or an applied pressure. Preferred pressure is from about 5 to about 50 atmospheres.

The molar ratio of ammonia to a phenol preferably ranges from about 1:1 to about 40:1, more preferably from about 3:1 to about 30:1.

Amination reaction of phenols according to the present invention may take place in either gas phase or liquid phase. The reaction is preferably carried out in gas phase in order to produce anilines in high selectivity and yield. The reaction may be carried out either continuous or batchwise. A continuous mode is preferred to economically produce a large amount of anilines on a commercial basis.

In the practice of the present invention, the liquid hourly space velocity (LHSV) is preferably set to about 0.01 to about 0.1 hr$^{-1}$, more preferably to about 0.02 to about 0.06 hr$^{-1}$. When a phenol is passed at an hourly flow rate (in liter/hour) to a reaction tower or column packed with a volume (in liter) of catalyst, the liquid hourly space velocity is the phenol flow rate divided by catalyst volume.

Reaction of a phenol with an amination agent according to the present invention is illustrated by referring to a continuous gas-phase reaction mode. A gaseous mixture is prepared by vaporizing a liquid phenol or phenols and liquid ammonia together or vaporizing them separately and then mixing, or vaporizing a heated phenol(s) with superheated ammonia. The resulting mixture is continuously admitted into a catalyst-loaded reactor at a temperature and pressure as previously described. The reaction mixture taken out of the outlet of the reactor is restored to atmospheric pressure and cooled. Since the reaction mixture contains a noticeable amount of ammonia dissolved therein, ammonia is separated by fractional distillation. The unreacted ammonia thus separated from the reaction mixture is recycled for reuse.

The reaction mixture removed of ammonia is subjected to distillation for water removal and then isolated into an aniline(s) and unreacted phenol(s). The aniline(s) is thus recovered while the unreacted phenol(s) is recycled to the reactor.

EXAMPLES

Examples of the present invention are given below by way of illustration and not by way of limitation.

EXAMPLE 1

A reactor of SUS 321 having an inner diameter of 25.0 mm and a length of 2 m was packed over an axial central portion with 660 ml of a γ-alumina catalyst in noodle shape having a diameter of 4 to 6 mm and a length of about 10 mm, consisting of 0.2% by weight of $Na_2O$, 0.02% by weight of $Fe_2O_3$, 0.06% by weight of $SiO_2$, and the remainder of $Al_2O_3$, and having the physical properties reported in Table 1. The reactor was heated to a predetermined temperature by a surrounding electric heater while passing ammonia gas. After the predetermined temperature was reached, phenol was supplied by means of a micro-metering pump.

Reaction was effected between ammonia and phenol under a pressure of 15 kg/cm$^2$-G. The feed rate of phenol was 0.045 hr$^{-1}$ in LHSV. Ammonia was fed in gas form with the molar ratio of ammonia to phenol set to 16:1.

The resulting reaction mixture was introduced from the outlet of the reactor into a liquid-gas separator where the liquid reaction product was collected. The liquid reaction product was a mixture of two liquids as it contained water resulting from amination reaction. With stirring, a predetermined volume was sampled out from the liquid. A predetermined volume of methanol was added to the sample to form a homogeneous phase.

The sample was subjected to quantitative determination by introducing 1 μl of the sample into a gas chromatograph having a column of SP-1000/Chromosolb WAW and computing the data according to the corrected areametric percentage method.

From the thus obtained composition of the reaction product, the rates of phenol conversion (Ph-C) and aniline selectivity (An-S) are computed according to the following equations:

Phenol conversion (%) =

$$\frac{\text{moles of phenol reacted per unit time}}{\text{moles of phenol fed per unit time}} \times 100$$

Aniline selectivity (%) =

$$\frac{\text{moles of aniline produced per unit time}}{\text{moles of phenol reacted per unit time}} \times 100$$

The activity of the catalyst in aminating phenol at varying reaction temperatures was reported in Table 1 as percent phenol conversion and aniline selectivity.

Separately, the catalyst of Example 1 was used in continuous operation for 180 days under a predetermined set of conditions, a reaction temperature of 400° C., an LHSV of phenol of 0.045 hr$^{-1}$, a reaction pressure of 15 kg/cm$^2$-G, and an ammonia/phenol molar ratio of 16. At the end of 180-day operation, the activity of the catalyst was determined in terms of phenol conversion (Ph-C) and aniline selectivity (An-S) to compare with the initial catalytic activity. The procedure was repeated by varying only the reaction temperature.

The results are shown in Table 2. No reduction in catalytic activity was observed.

TABLE 2

| | Catalyst Life Test | | | | |
|---|---|---|---|---|---|
| | Reaction | Initial | | After 180 days | |
| Catalyst | temperature | Ph-C | An-S | Ph-C | An-S |
| Example 1 | 360° C. | 82.8% | 99.6% | 87.0% | 99.5% |
| | 370° C. | 99.7% | 99.2% | 99.7% | 99.2% |
| | 380° C. | 99.8% | 98.9% | 99.8% | 98.9% |

EXAMPLE 2

Using a noodle shaped catalyst of the same composition and shape as in Example 1 except for the physical properties shown in Table 1, amination of phenol was carried out in the same reactor under the same reaction conditions as in Example 1.

The results of an activity test were shown in Table 1.

EXAMPLE 3

Using a spherical catalyst of the same composition as in Example 1, but having a diameter of 6 to 7 mm and the physical properties shown in Table 1, amination of phenol was carried out in the same reactor under the same reaction conditions as in Example 1.

The results of an activity test were shown in Table 1.

Separately, the catalyst of Example 3 was used in continuous operation for 180 days under a predetermined set of conditions, a reaction temperature of 400° C., an LHSV of phenol of 0.045 hr$^{-1}$, a reaction pressure of 15 kg/cm$^2$-G, and an ammonia/phenol molar ratio of 16. At the end of 180-day operation, the activity of the catalyst was determined in terms of phenol conversion (Ph-C) and aniline selectivity (An-S) to compare with the initial catalytic activity. The procedure was repeated by vaying only the reaction temperature.

The results are shown in Table 3. No reduction in catalytic activity was observed.

TABLE 3

| Catalyst | Reaction temperature | Initial Ph-C | Initial An-S | After 180 days Ph-C | After 180 days An-S |
|---|---|---|---|---|---|
| Example 3 | 360° C. | 83.3% | 99.5% | 88.0% | 99.5% |
|  | 370° C. | 99.5% | 99.1% | 99.6% | 99.2% |
|  | 380° C. | 99.7% | 98.8% | 99.7% | 98.9% |

EXAMPLE 4

Amination of phenol was carried out in the same reactor under the same reaction conditions as in Example 1 except that the catalyst used was a spherical γ-alumina catalyst with a diameter of 6 to 7 mm, consisting of 0.4% by weight of $Na_2O$, 0.02% by weight of $Fe_2O_3$, 2.7% by weight of $SiO_2$, 90.6% by weight of $Al_2O_3$, and 6.0% by weight of L.O.I. (Loss on Ignition) and having the physical properties shown in Table 1.

The results of an activity test were shown in Table 1.

COMPARATIVE EXAMPLE 1

Amination of phenol was carried out in the same reactor under the same reaction conditions as in Example 1 except that the catalyst used was a γ-alumina catalyst in noodle shape having a diameter of 4 to 6 mm and a length of about 10 mm, consisting of 0.17% by weight of $Na_2O$, 0.02% by weight of $Fe_2O_3$, 0.06% by weight of $SiO_2$, and the remainder of $Al_2O_3$ on dry basis, and having the physical properties reported in Table 1.

The results of an activity test were shown in Table 1.

COMPARATIVE EXAMPLE 2

Amination of phenol was carried out in the same reactor under the same reaction conditions as in Example 1 except that the catalyst used was a γ-alumina catalyst in noodle shape having a diameter of 4 to 6 mm and a length of about 10 mm, consisting of 0.17% by weight of $Na_2$, 0.02% by weight of $Fe_2O_3$, 0.06% by weight of $SiO_2$, and the remainder of $Al_2O_3$ on dry basis, and having the physical properties reported in Table 1.

The results of an activity test were shown in Table 1.

COMPARATIVE EXAMPLE 3

Amination of phenol was carried out in the same reactor under the same reaction conditions as in Example 1 except that the catalyst used was a spherical γ-alumina catalyst with a diameter of 6 to 7 mm, consisting of 0.4% by weight of $Na_2O$, 0.03% by weight of $Fe_2O_3$, 10.5% by weight of $SiO_2$, 84.8% by weight of $Al_2O_3$, and 4.3% by weight of L.O.I. and having the physical properties shown in Table 1.

The results of an activity test were shown in Table 1.

COMPARATIVE EXAMPLE 4

Amination of phenol was carried out in the same reactor under the same reaction conditions as in Example 1 except that the catalyst used was a spherical γ-alumIna catalyst with a diameter of 6 to 7 mm, consisting of 0.3% by weight of $Na_2O$, 0.03% by weight of $Fe_2O_3$, 0.02% by weight of $SiO_2$, 95.4% by weight of $Al_2O_3$, and 4.3% by weight of L.O.I. and having the physical properties shown in Table 1.

The results of an activity test were shown in Table 1.

COMPARATIVE EXAMPLE 5

Amination of phenol was carried out in the same reactor under the same reaction conditions as in Example 1 except that the catalyst used was a spherical γ-alumina catalyst with a diameter of 6 to 7 mm, consisting of 0.4% by weight of $Na_2O$, 0.01% by weight of $Fe_2O_3$, and the remainder of $Al_2O_3$ on dry basis and having the physical properties shown in Table 1.

The results of an activity test were shown in Table 1.

TABLE 1

Catalyst's Physical Properties and Activity
(Reaction conditions: LHSV (Phenol) = 0.045 $hr^{-1}$; $NH_3$/Phenol (mol ratio) = 16; Pressure = 15 kg/$cm^2$ G)

| | Shape (Pore structure) | Specific surface area ($m^2$/g) | Total pore volume (cc/g) | Mean pore diameter (Å) | $\sigma_n$ (Å) | Acid Strength Distribution (Integrated Acid quantity) *1 | | | | |
|---|---|---|---|---|---|---|---|---|---|---|
| | | | | | | pKa ≦ 6.8 (meq/g) | pKa ≦ 4.8 (meq/g) | pKa ≦ 3.3 (meq/g) | pKa ≦ 1.5 (meq/g) | pKa ≦ 3.0 (meq/g) |
| E1 | Noodle (Ink bottle) | 275 | 0.66 | 69 | 13 | 0.31 | 0.08 | 0 | 0 | 0 |
| E2 | Noodle (Ink bottle) | 266 | 0.72 | 80 | 21 | 0.32 | 0.10 | 0.06 | 0 | 0 |
| E3 | Spherical (Ink bottle) | 280 | 0.61 | 60 | 15 | 0.26 | 0.03 | 0 | 0 | 0 |
| E4 | Spherical (Ink bottle) | 223 | 0.46 | 53 | 25 | 0.26 | 0.03 | 0 | 0 | 0 |
| CE1 | Noodle (Ink bottle) | 225 | 0.82 | 120 | 24 | 0.22 | 0.04 | 0.02 | 0 | 0 |
| CE2 | Noodle (Ink bottle) | 205 | 0.90 | 161 | 24 | 0.14 | 0 | 0 | 0 | 0 |
| CE3 | Spherical (Slit) | 125 | 0.43 | 101 | 53 | 0.31 | — | 0.16 | 0.16 | 0.16 |
| CE4 | Spherical (Slit) | 83 | 0.30 | 113 | 55 | 0.28 | 0.07 | 0 | 0 | 0 |
| CE5 | Spherical (Slit) | 317 | 0.30 | 50 | 20 | not measured | | | | |

| | Catalytic Activity | | | | | |
|---|---|---|---|---|---|---|
| | Phenol conversion (%) | | | Aniline selectivity (%) | | |
| | 360° C. | 370° C. | 380° C. | 360° C. | 370° C. | 380° C. |
| E1 | 82.8 | 99.7 | 99.8 | 99.6 | 99.2 | 98.9 |
| E2 | 71.4 | 94.9 | 99.8 | 99.7 | 99.4 | 99.1 |

TABLE 1-continued

Catalyst's Physical Properties and Activity
(Reaction conditions: LHSV (Phenol) = 0.045 hr$^{-1}$; NH$_3$/
Phenol (mol ratio) = 16; Pressure = 15 kg/cm$^2$ G)

| | | | | | | |
|---|---|---|---|---|---|---|
| E3 | 83.3 | 99.6 | 99.7 | 99.5 | 99.1 | 98.8 |
| E4 | 99.6 | 99.8 | 99.7 | 99.6 | 99.2 | 98.9 |
| CE1 | — | 80.6 | 99.4 | — | 99.6 | 99.4 |
| CE2 | — | 74.6 | 94.4 | — | 99.7 | 99.5 |
| CE3 | — | 75.2 | 94.9 | — | 99.0 | 98.6 |
| CE4 | — | 88.0 | 98.8 | — | 98.9 | 98.7 |
| CE5 | — | — | 28.7 | — | — | 99.9 |

*1 Integrated quantity of acid having a pKa of up to the indicated value is expressed in meq/gram.

As understood from the above teachings, according to the present invention, an aniline is prepared by reacting a phenol with an amination agent in the presence of a γ-alumina catalyst having a mean pore diameter in the range of from 30 to 90 Å with a standard deviation of 10 to 40 Å based on statistic calculation from pore diameter and pore volume. Preferably, the γ-alumina catalyst contains ink bottle-shaped pores in a total pore volume of at least 0.4 c.c./gram on dry basis. Also preferably, the γ-alumina catalyst is a weakly acidic alumina having a pKa value in the range of from +3.3 to +6.8 as measured with Hammett's indicator and an integrated acid quantity of up to 0.5 meq/gram on dry basis. Also preferably, the γ-alumina catalyst is a low alkali alumina consisting essentially of at least 90% by weight of alumina, less than 10% by weight of silica, and up to 0.5% by weight of an alkali metal oxide in dry state. The catalyst of this nature can catalyze formation of anilines in higher yields and selectivity than with the prior art well-known catalysts even when reaction is carried out at a lower temperature. Low reaction temperatures provide an increased selectivity of an aniline and control formation of carbonaceous or resinous substances due to degradation of the aniline. Therefore, the catalyst of the present invention has a great advantage that its catalytic activity is maintained high for an extended period of time.

We claim:

1. A process for preparing an niline, comprising reacting a phenol with an amination agent in the presence of a gamma-alumina catalyst wherein said gamma-alumina catalyst is, without pretreatment, a low alkali alumina consisting essentially of at least 90% by weight of alumina, less than 10% by weight of silica, and up to pb 0.5% by weight of an alkali metal oxide in the dry state, said catalyst has, without pretreatment, a mean pore diameter in the range of from 30 to 90 angstroms with a standard deviation of 10 to 40 angstroms based on statistical calculation from the pore diameter and pore volume, and said gamma-alumina catalyst is, without pretreatment, a weakly acidic alumina having a pKa value in the range of from +3.3 to +6.8 as measured with Hammett's indicator and an integrated acid quantity of up to 0.5 meq/gram on the dry basis.

2. The process as set forth in claim 1 wherein said γ-alumina catalyst contains ink bottle-shaped pores in a total pore volume of at least 0.4 c.c./gram on the dry basis.

* * * * *